US009587834B2

(12) United States Patent
DeSilva et al.

(10) Patent No.: US 9,587,834 B2
(45) Date of Patent: Mar. 7, 2017

(54) FLASHBACK DETECTION IN GAS TURBINE ENGINES USING DISTRIBUTED SENSING

(71) Applicant: Siemens Energy, Inc., Orlando, FL (US)

(72) Inventors: Upul P. DeSilva, Oviedo, FL (US); Christine P. Spiegelberg, Winter Park, FL (US)

(73) Assignee: SIEMENS ENERGY, INC., Orlando, FL (US)

( * ) Notice: Subject to any disclaimer, the term of this patent is extended or adjusted under 35 U.S.C. 154(b) by 409 days.

(21) Appl. No.: 14/179,758

(22) Filed: Feb. 13, 2014

(65) Prior Publication Data
US 2015/0226436 A1    Aug. 13, 2015

(51) Int. Cl.
| | |
|---|---|
| F23D 14/82 | (2006.01) |
| F23R 3/28 | (2006.01) |
| F02C 7/22 | (2006.01) |
| G01M 15/14 | (2006.01) |
| G01N 21/53 | (2006.01) |

(Continued)

(52) U.S. Cl.
CPC ............... F23R 3/286 (2013.01); F02C 7/22 (2013.01); F23D 14/82 (2013.01); F23N 5/082 (2013.01); F23R 3/002 (2013.01); F23R 3/283 (2013.01); F23R 3/42 (2013.01); G01M 15/14 (2013.01); G01N 21/53 (2013.01);
(Continued)

(58) Field of Classification Search
CPC ......... G01K 11/32; G01N 21/88; F23R 3/286; F23N 5/082; F05D 2270/804; F02C 9/28; F02C 9/46; F02C 9/26
See application file for complete search history.

(56) References Cited

U.S. PATENT DOCUMENTS

| | | | |
|---|---|---|---|
| 2007/0119147 A1* | 5/2007 | Cornwell | F01D 17/02 60/39.281 |
| 2007/0171425 A1* | 7/2007 | De Groot | G03F 7/70775 356/478 |

(Continued)

FOREIGN PATENT DOCUMENTS

| | | |
|---|---|---|
| EP | 2120028 A1 | 11/2009 |
| WO | 2013006410 A2 | 1/2013 |
| WO | WO 2013006410 A2 * | 1/2013 ............ F01D 21/003 |

OTHER PUBLICATIONS

D.K. Gifford et al., "Distributed Fiber-Optic Temperature Sensing using Rayleigh Backscatter," 31st European Conf. and Exhibition Optical Communications, Glasgow, Scotland, 2005, vol. 3, pp. 511-512.

*Primary Examiner* — Jason L Vaughan
*Assistant Examiner* — Amanda Meneghini

(57) ABSTRACT

A distributed sensing system for detecting a flashback condition in a combustor for a gas turbine engine The distributed sensing system includes one or more strategically positioned fiber optic cables provided upstream of the combustion area in the combustor. The distributed sensing system employs Rayleigh backscattering and swept-wavelength interferometry to measure temperature and reliably identify the location of the flashback condition The fiber optic cable is specially fabricated to have a high temperature resistance suitable for those temperatures existing during flashback conditions. The fiber optic cable can be wrapped on an inside of a combustion basket or on an outside of the combustion basket, and in a serpentine manner or otherwise.

16 Claims, 3 Drawing Sheets

(51) Int. Cl.
*F23N 5/08* (2006.01)
*F23R 3/00* (2006.01)
*F23R 3/42* (2006.01)

(52) U.S. Cl.
CPC ...... *F05D 2220/32* (2013.01); *F05D 2260/83* (2013.01); *F05D 2270/804* (2013.01)

(56) References Cited

U.S. PATENT DOCUMENTS

2011/0273719 A1* 11/2011 Froggatt ............... G01M 11/35
 356/446
2012/0174590 A1* 7/2012 Krull ....................... F23N 5/082
 60/772

* cited by examiner

FLASHBACK DETECTION IN GAS TURBINE ENGINES USING DISTRIBUTED SENSING

BACKGROUND OF THE INVENTION

Field of the Invention

This invention relates generally to a system and method for detecting flashback events in a combustor of a gas turbine engine and, more particularly, to a fiber optic distributed sensing system employing Rayleigh backscattering and swept-wavelength interferometry for measuring temperature and detecting flashback events at many locations within a combustor of a gas turbine engine.

Discussion of the Related Art

The world's energy needs continue to rise which provides a demand for reliable, affordable, efficient and environmentally-compatible power generation. A gas turbine engine is one known machine that provides efficient power, and often has application for an electric generator in a power plant, or engines in an aircraft or a ship. A typically gas turbine engine includes a compressor section, a combustion section and a turbine section. The compressor section provides a compressed airflow to the combustion section where the air is mixed with a fuel, such as natural gas. The combustion section includes a plurality of circumferentially disposed combustors that receive the fuel to be mixed with the air and ignited to generate a working gas. The working gas expands through the turbine section and is directed across rows of blades therein by associated vanes As the working gas passes through the turbine section, it causes the blades to rotate, which in turn causes a shaft to rotate, thereby producing mechanical work Each combustor includes a fuel injector, orifices for receiving compressed air and an igniter for igniting the fuel/air mixture to create a flame in a combustion basket The pressure and volume of both the injected fuel and the air are carefully controlled for a particular combustor so that the flame is propelled forward into a transition duct to the turbine section. As the operating conditions of the turbine engine vary and change, a failure mode could occur where the pressure and flow volume of the fuel and/or air causes a flashback condition where the flame travels backwards in a direction away from the turbine section. If the engine operating parameters are not immediately changed to remove the flashback condition, the flame flashback could cause damage to components upstream of the combustion area in the combustion basket because many of those components are not designed for such high temperatures.

It is known in the art to provide various types of sensors, such as high temperature thermocouples or optical detectors, such as fiber Bragg grating (FBG) sensors, strategically positioned behind the combustion area in the combustion basket of a combustor to detect flame flashback by detecting higher than normal temperatures. If flame flashback is detected by one of the detectors, then the system engine controller will take some immediate action, possibly system shutdown, to remove the flashback condition. However, the number of thermocouples and/or optical sensors that can be provided in the combustor is limited because of limits of the ability to configure and position multiple thermocouple sensors in the combustion basket or the spatial resolution of the optical detectors provided in an optical sensor. Because the resolution is limited, the ability to quickly detect a flashback condition and specifically identify the location of the flashback condition is correspondingly limited. For example, the flame may flash back to a location in the combustion basket where a sensor does not exist, thus limiting the ability to detect that flashback condition.

SUMMARY OF THE INVENTION

The present disclosure describes a distributed sensing system for detecting a flashback condition in a combustor for a gas turbine engine, where the system is based on Rayleigh backscattering that can be detected at a very high spatial resolution The distributed sensing system employs swept-wavelength interferometry to measure temperature using the Rayleigh backscattering and reliably identify the location of the flashback condition. A fiber optic cable supporting the Rayleigh backscattering is specially fabricated to have a high temperature resistance suitable for those temperatures existing during flashback conditions. The fiber optic cable can be wrapped on an inside of a combustion basket or on an outside of the combustion basket, and in a serpentine manner or otherwise Additional features of the present invention will become apparent from the following description and appended claims, taken in conjunction with the accompanying drawings.

DETAILED DESCRIPTION OF THE EMBODIMENTS

The following discussion of the embodiments of the invention directed to a distributed sensing system employing a fiber optic cable and Rayleigh backscattering for detecting temperature and a flashback condition in a combustor for a gas turbine engine is merely exemplary in nature, and is in no way intended to limit the invention or its applications or uses.

Figure 1:
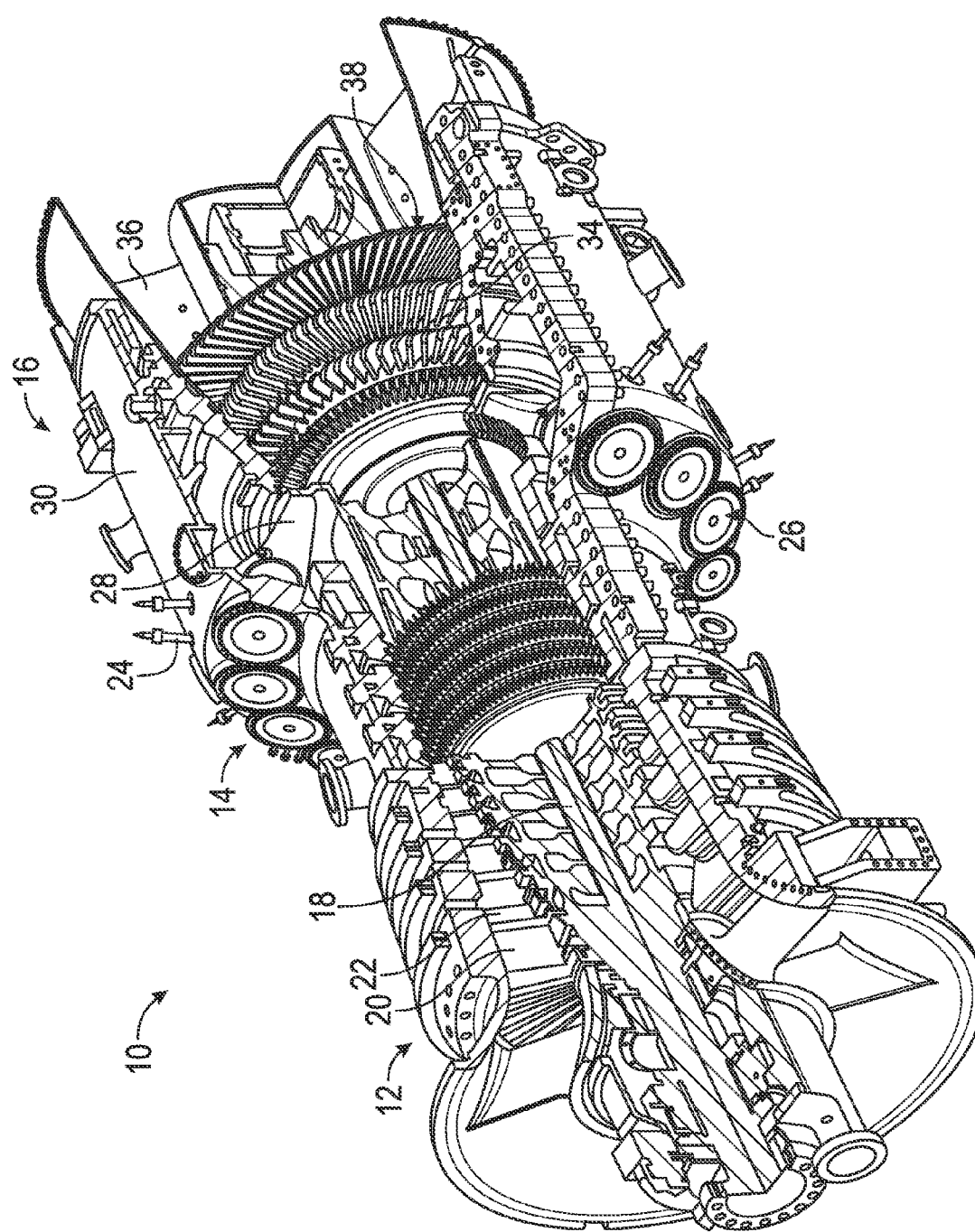
FIG. 1 is a cut-away, isometric view of a gas turbine engine.

FIG. 1 is a cut-away, isometric view of a gas turbine engine 10 including a compressor section 12, a combustion section 14 and a turbine section 16 all enclosed within an outer housing or casing 30, where operation of the engine 10 causes a central shaft or rotor 18 to rotate, thus creating mechanical work. The engine 10 is illustrated and described by way of a non-limiting example to provide context to the invention discussed below. Those skilled in the art will appreciate that other gas turbine engine designs can also be used in connection with the invention Rotation of the rotor 18 draws air into the compressor section 12 where it is directed by vanes 22 and compressed by rotating blades 20 to be delivered to the combustion section 14, where the compressed air is mixed with a fuel, such as natural gas, and where the fuel/air mixture is ignited to create a hot working gas. More specifically, the combustion section 14 includes a number of circumferentially disposed combustors 26 each receiving the fuel that is injected into the combustor 26 by an injector (not shown), mixed with the compressed air and ignited by an igniter 24 to be combusted to create the working gas, which is directed by a transition component 28 into the turbine section 16. The working gas is then directed by circumferentially disposed stationary vanes (not shown in FIG. 1) in the turbine section 16 to flow across circumferentially disposed rotatable turbine blades 34, which causes the turbine blades 34 to rotate, thus rotating the rotor 18. Once the working gas passes through the turbine section 16 it is output from the engine 10 as an exhaust gas through an output nozzle 36.

Each group of the circumferentially disposed stationary vanes defines a row of the vanes and each group of the circumferentially disposed blades 34 defines a row 38 of the blades 34. In this non-limiting embodiment, the turbine section 16 includes four rows 38 of the rotating blades 34 and four rows of the stationary vanes in an alternating sequence. In other gas turbine engine designs, the turbine section 16 may include more or less rows of the turbine blades 34 It is noted that the most forward row of the turbine blades 34, referred to as the row 1 blades, and the vanes, referred to as the row 1 vanes, receive the highest temperature of the working gas, where the temperature of the working gas decreases as it flows through the turbine section 16.

Figure 2:
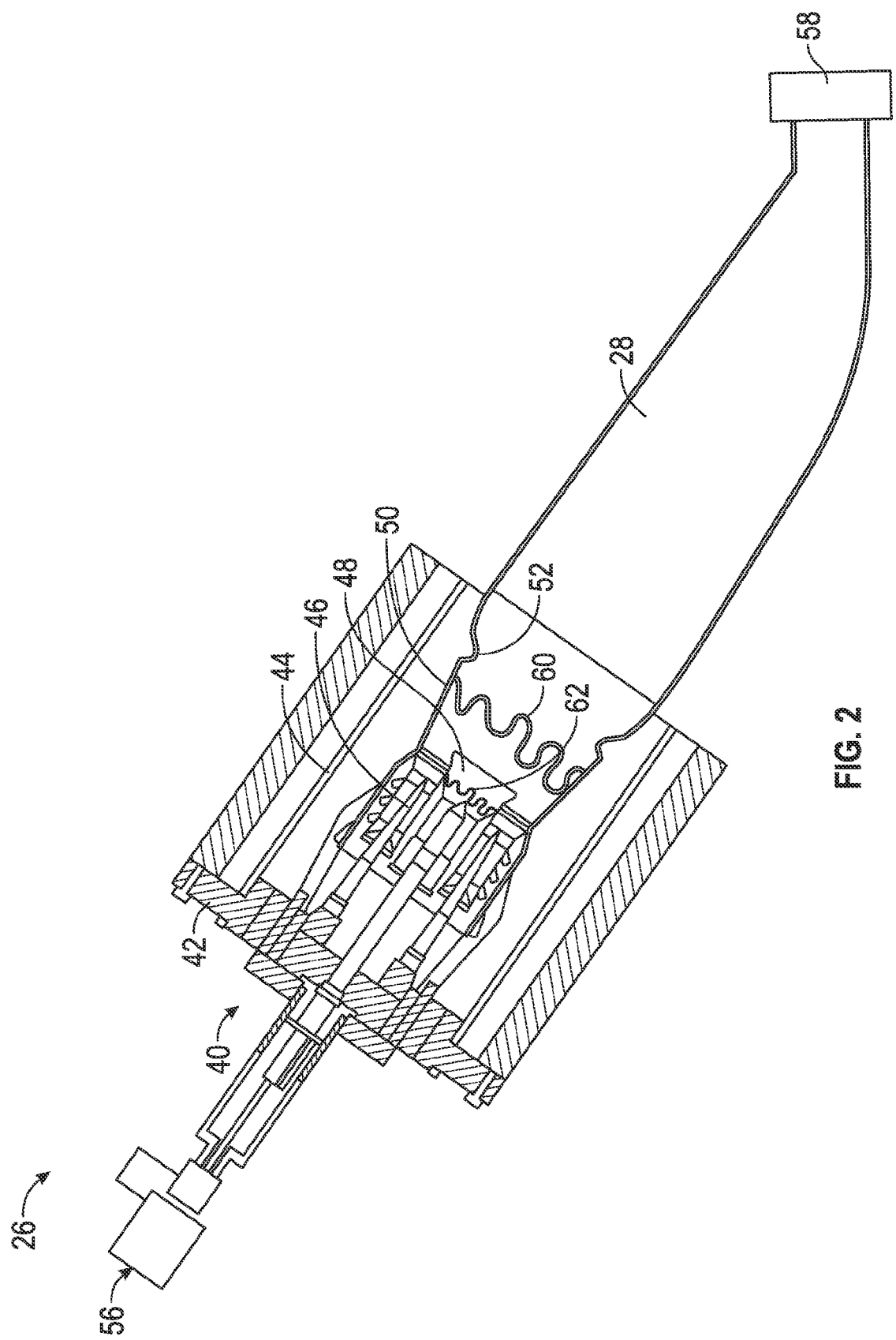
FIG. 2 is a cut-away, cross-sectional type view of a portion of a combustor in the combustion section of the gas turbine engine.

FIG. 2 is a cut-away, cross-sectional type view of a portion of one of the combustors 26 coupled to one of the transition components 28. The combustor 26 includes a fuel injection system 40 mounted to a cover plate 42 enclosing a combustion shell 44. The fuel injection system 40 includes fuel nozzles 46 and a pilot nozzle 48 An end of the fuel injection system 40 proximate the pilot nozzle 48 is coupled to a funnel-shaped combustion basket 50 including orifices 52 that allow pressurized air from the compressor section 12 to enter the combustion basket 50. A combustion monitoring and control system 56 controls the fuel injection system 40 to cause the desired amount of fuel to be injected into the combustion basket 50 through the fuel nozzles 46 for a particular operating condition of the engine, where the fuel is mixed with the air and is ignited by the pilot flame to provide a high intensity flame. The flame generates the hot working gas that flows through the transition component 28 towards the first row of vanes in the turbine section 16, represented here by vane 58.

The present invention proposes a distributed sensing system that employs swept-wavelength interferometry for detecting Rayleigh backscattering in a fiber optical cable to detect elevated temperatures in a region in the combustor 26 upstream from the location where the fuel/air is ignited in the combustion basket 50 to generate the hot working gas, which could be an indication of a flashback condition. The distributed sensing system includes one or more fiber optic cables of a certain length strategically coupled to the combustion basket 50, the pilot nozzle 48, or some other suitable location in the combustor 26. In this non-limiting example, a sensing fiber optic cable 60 is mounted to an inside surface of the combustion basket 50 upstream of the orifices 52 and thus upstream of the location where the main combustion event occurs. Additionally, or alternately, a distributed sensing fiber optic cable 62 is provided within the pilot nozzle 48. The cables 60 and 62 provide Rayleigh backscatter reflectometry that will be measured using swept wavelength interferometry. In one non-limiting embodiment, the fiber 60 is about 1 meter long which can provide sub-millimeter spatial resolution and a high accuracy with a fast response time.

Figure 3:
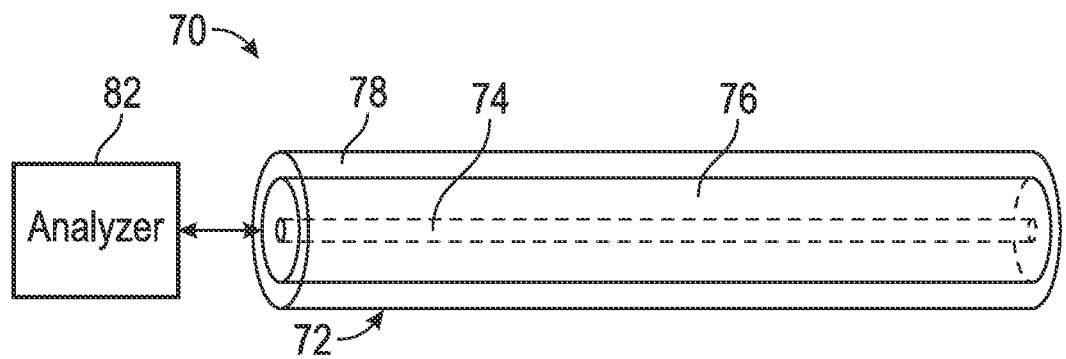
FIG. 3 is an illustration of a distributed sensing system including a fiber optic cable.

The fiber 60 can be mounted to the combustion basket 50, or other suitable combustor component, in any desired strategic manner that allows it to effectively detect temperature depending on the particular combustor design. For example, the fiber 60 can be wound around an internal surface of the combustion basket 50 or wound around an external surface of the combustion basket 50. Further, the cable 60 can be mounted to the inside or outside wall of the combustion basket 50 in a serpentine manner to provide even a higher degree of resolution for a particular application. By providing a single fiber in this manner, and internal to the combustion basket 50, only a single hole needs to be drilled into the wall of the combustion basket 50 to allow the cable 60 to placed therein, where as with the tradition thermocouple sensors, a separate hole needed to be drilled for each separate thermocouple sensor The fiber optical cable 60 can be mounted to the wall of the combustion basket 50 in any suitable manner, such as by a high temperature adhesive or thermo-bonding FIG. 3 is a representation of a distributed sensing system 70 including a distributed sensing fiber optic cable 72 of the type that can be used for the fiber optic cables 60 and 62 discussed above The fiber optic cable 72 includes an optical fiber core 74 surrounded by an outer cladding layer 76. The index of refraction of the cladding layer 76 is greater than the index of refraction of the fiber core 74 so that a light beam at a low enough angle of incidence propagating down the fiber core 74 is reflected off of the transition between the fiber core 74 and the cladding layer 76 and is trapped therein. In one embodiment, the fiber core 74 is about 10 μm in diameter, which provides a multi-mode fiber for propagating multiple optical modes. Because the fiber optic cable 72 will be used in a high temperature environment, the fiber optic cable 72 is made of a high temperature material, such as quartz, so as not to be damaged in the high temperature environment. Further heat resistance can be provided by coating the cladding layer 76 with a high temperature coating 78, such as gold, so as to withstand temperatures up to about 800° C.

Figure 4:
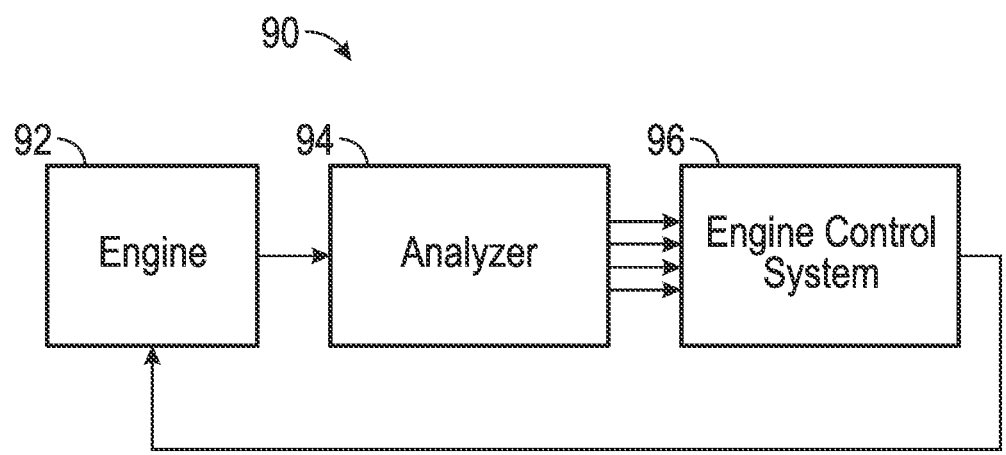
FIG. 4 is a block diagram of a flashback engine control system.

The general idea of employing swept wavelength interferometry for detecting Rayleigh backscattering along the length of a fiber optic cable to detect temperature change is known to those skilled in the art. An analyzer 82 includes a swept wavelength interferometer having an optical reference path of a known length and an optical sensing path, which is the fiber optic cable 72 The analyzer 82 sends an optical signal of a predetermined wavelength down the core 74. Rayleigh backscattering of the optical signal as it propagates along the cable 72 is caused by random profile fluctuations along the length of the cable 72. The temperature of the cable 72 creates a particular reflection spectrum of the backscattering along the length of the fiber cable 72, where changes in the temperature of the cable 72 cause a shift in that spectrum. The profile of the backscattering spectrum can be analyzed in segments along the length of the fiber cable 72 by Fourier transforming the spectrum to give the spatial resolution In one non-limiting embodiment, the backscattering analysis can provide a spatial resolution of about 0.5 mm and the analyzer response time of about 0.1 seconds FIG. 4 is a block diagram of a distributed sensing control system 90 for responding to a flame flashback condition as discussed above. The system 90 includes a box 92 representing the gas turbine engine, which provides a signal to an analyzer 94 representing the optical signal from the distributed sensing fiber cable. Based on the numerous reflections from the sensing locations in the fiber optic cable, the analyzer 94 is able to determine if flame flashback is occurring, and if so, the location of the flashback, the intensity of the flashback and the rate of propagation of the flashback The analyzer 94 provides a signal indicative of all of these parameters to an engine control system 96 that will change the operating parameters of the engine 92, including shutting the engine 92 down, if necessary, to limit the flashback condition if it exists. The engine control system 96 likely will provide a signal to the combustion monitoring and control system 56 for the particular combustor 26 that is experiencing the flashback condition.

The foregoing discussion discloses and describes merely exemplary embodiments of the present invention. One skilled in the art will readily recognize from such discussion, and from the accompanying drawings and claims, that various changes, modifications and variations can be made therein without departing from the scope of the invention as defined in the following claims

What is claimed is:

1. A combustor for a gas turbine engine, said combustor comprising:
   a fuel injection system for injecting fuel into the combustor;
   a combustion monitoring and control system for monitoring and controlling the injection of the fuel into the combustor;
   a combustion basket responsive to the fuel from the fuel injection system and air, said fuel and air being mixed and combusted in the combustion basket to generate a hot working gas; and
   a distributed sensing system including at least one fiber optic cable and an analyzer, the analyzer including a swept wavelength interferometer having an optical reference path of a known length, said analyzer providing an optical signal propagating down the fiber optic cable and receiving a Rayleigh backscattering spectrum therefrom, said analyzer providing temperature monitoring along the length of the fiber cable using the Rayleigh backscattering spectrum to determine whether a flame flashback condition is occurring in the combustor, and wherein the analyzer provides a control signal to the combustion monitoring and control system to control the injection of the fuel if the flame flashback condition is detected.

2. The combustor according to claim 1 wherein the fiber optic cable is wrapped around an inside surface of the combustion basket.

3. The combustor according to claim 1 wherein the fiber optic cable is wrapped around an outside surface of the combustion basket.

4. The combustor according to claim 1 wherein the fiber optic cable is mounted to the combustion basket in a serpentine manner.

5. The combustor according to claim 1 wherein the at least one fiber optic cable is a high temperature resistant fiber optic cable.

6. The combustor according to claim 5 wherein the high temperature resistant fiber optic cable includes a quartz core, a quartz cladding layer and an outer coating of a high temperature resistant material.

7. The combustor according to claim 1 wherein the fuel injection system includes a pilot nozzle, said distributed sensing system including another fiber optic cable positioned on the pilot nozzle.

8. The combustor according to claim 1 wherein the analyzer provides an indication of flashback location, flashback intensity and flashback rate of propagation.

9. The combustor according to claim 1 wherein the analyzer provides an equal or better location resolution of 0.5 mm and a 0.1 second response time.

10. A combustor for a gas turbine engine, said combustor comprising:
    a fuel injection system for injecting fuel into the combustor;
    a combustion monitoring and control system for monitoring and controlling the injection of the fuel into the combustor;
    a combustion basket responsive to the fuel from the fuel injection system and air, said fuel and air being mixed and combusted in the combustion basket to generate a hot working gas; and
    a distributed sensing system including at least one high temperature resistant fiber optic cable coupled to the combustion basket, said distributed sensing system further including an analyzer providing an optic signal propagating down the fiber optic cable and receiving a Rayleigh backscattering spectrum therefrom, said analyzer including a swept-wavelength interferometer having an optical reference path of a known length employing swept-wavelength interferometry to determine temperature along the length of the fiber cable to determine whether a flashback condition is occurring, wherein the analyzer provides an indication of flashback location, flashback intensity and flashback rate of propagation, said analyzer providing a control signal to the combustion monitoring and control system to control the injection of the fuel if the flame flashback condition is detected.

11. The combustor according to claim 10 wherein the fiber optic cable is wrapped around an inside surface of the combustion basket.

12. The combustor according to claim 10 wherein the fiber optic cable is wrapped around an outside surface of the combustion basket.

13. The combustor according to claim 10 wherein the fiber optic cable is mounted to the combustion basket in a serpentine manner.

14. The combustor according to claim 10 wherein the at least one fiber optic cable is able to withstand temperatures equal to or better than 800° C.

15. The combustor according to claim 10 wherein the at least one high temperature resistant fiber optic cable includes a quartz core, a quartz cladding layer and an outer coating of a high temperature resistant material.

16. The combustor according to claim 10 wherein the fuel injection system includes a pilot nozzle, said distributed sensing system including another fiber optic cable positioned on the pilot nozzle.

* * * * *